United States Patent
Lege et al.

(10) Patent No.: US 7,186,403 B2
(45) Date of Patent: Mar. 6, 2007

(54) FATTY ESTER MIXTURE FOR SOLAR PROTECTION AND COSMETIC PRODUCT CONTAINING SAME

(75) Inventors: Corinne Lege, Nanterre (FR); Nathalie Loubat, Garches (FR)

(73) Assignee: Stearinerie Dubois Fils, Le Blanc (FR)

( * ) Notice: Subject to any disclaimer, the term of this patent is extended or adjusted under 35 U.S.C. 154(b) by 0 days.

(21) Appl. No.: 10/220,264

(22) PCT Filed: Mar. 12, 2001

(86) PCT No.: PCT/FR01/00724

§ 371 (c)(1),
(2), (4) Date: Sep. 6, 2002

(87) PCT Pub. No.: WO01/68050

PCT Pub. Date: Sep. 20, 2001

(65) Prior Publication Data

US 2003/0031635 A1    Feb. 13, 2003

(30) Foreign Application Priority Data

Mar. 13, 2000  (FR) .................................. 00 03158

(51) Int. Cl.
- *A61K 8/00* (2006.01)
- *A61K 8/18* (2006.01)
- *A61K 8/36* (2006.01)
- *A61K 8/02* (2006.01)
- *A61K 8/49* (2006.01)

(52) U.S. Cl. .................... 424/59; 424/60; 424/70.9; 424/401; 514/785

(58) Field of Classification Search ............... 424/401, 424/59, 70.9, 60; 514/785
See application file for complete search history.

(56) References Cited

U.S. PATENT DOCUMENTS

| 4,424,234 | A | * | 1/1984 | Alderson et al. ............ 514/558 |
| 4,797,273 | A | * | 1/1989 | Linn et al. .................... 424/59 |
| 5,008,100 | A | * | 4/1991 | Zecchino et al. ............. 424/59 |
| 5,039,516 | A | * | 8/1991 | Goodman et al. ............ 424/59 |
| 5,876,736 | A | * | 3/1999 | Cohen et al. ................ 424/401 |
| 6,165,449 | A | * | 12/2000 | George et al. ................ 424/59 |

FOREIGN PATENT DOCUMENTS

| EP | 0416837 A1 * | 3/1991 |
| FR | 2 789 308 | 8/2000 |
| WO | WO 95/00107 | 1/1995 |

* cited by examiner

*Primary Examiner*—Sreeni Padmanabhan
*Assistant Examiner*—Marina Lamm
(74) *Attorney, Agent, or Firm*—Jacobson Holman PLLC

(57) ABSTRACT

The invention concerns a fatty ester mixture for cosmetic product, comprising at least two fatty esters selected among a branched C4–C8 mono carboxylic acid and a branched C8–C12 alcohol, the esters of a C8–C12 dicarboxylic acid the esters of a linear C8–C12 dicarboxylic acid and a branched C3–C6 alcohol and the esters of a hydroxycarboxylic acid and a linear C10–C18 alcohol. The invention is useful in cosmetics and more particularly for solar protection products.

5 Claims, No Drawings

FATTY ESTER MIXTURE FOR SOLAR PROTECTION AND COSMETIC PRODUCT CONTAINING SAME

The invention relates to a mixture of fatty esters, inter alia for a cosmetic product containing at least one sun filter such as a sunscreen product, and to a cosmetic product comprising the said mixture of fatty esters.

Cosmetic skin products are available in various forms including emulsions or oil. Some of these products can comprise a combination of ultraviolet-filtering substances.

It will be recalled that ultraviolet filtering substances are adapted to protect the skin against the risk of serious sunburn.

Known mixtures of fatty esters solubilise sun filters and also assist the cosmetic product to spread over the skin so as to obtain a uniform protective cover. Cosmetic products also comprise waxes, surfactants, fatty substances (other than fatty esters) including mineral or vegetable oils, silicones, perfumes, anti-oxidants, active principles, dyes, pigments, thickeners, texturing agents etc in proportions varying inter alia with the desired qualities of the resulting cosmetic product.

A cosmetic product may be defined via its "sun protection factor" SPF. The present trend, inter alia as regards sun protection factors, is to improve the said factor.

Among known products for forming a mixture of fatty substances, frequent use is made of $C_{12}$–$C_{15}$ benzoate, usually in association with volatile silicones.

However there are other known fatty substances such as those cited in the document U.S. Pat. No. 4,940,574A, all of which are known for their capacity to solubilise filter products and for their effect in spreading the cosmetic product.

One aim of the invention is to provide a mixture of fatty esters which performs the said functions but also has a favourable effect on the sun protection factor (SPF).

Another aim is to provide a said mixture of fatty esters for preparing a high-performance cosmetic product at reasonable cost.

These aims, together with others which will appear hereinafter, are achieved by a mixture of fatty esters inter alia for a cosmetic product, characterised according to the invention in that it comprises at least two fatty esters chosen from among esters of a $C_4$–$C_8$ branched monocarboxylic acid and a $C_8$–$C_{12}$ branched alcohol, esters of a $C_8$–$C_{12}$ straight-chain dicarboxylic acid and a $C_3$–$C_6$ branched alcohol, and esters of a hydroxycarboxylic acid and a $C_{10}$–$C_{18}$ straight-chain alcohol.

Advantageously, the isodecyl ester of 2,2-dimethyl propionic acid is chosen from among esters of a $C_4$–$C_8$ branched monocarboxylic acid and a $C_8$–$C_{12}$ branched alcohol.

Preferably, the isopropyl ester of decanedioic acid is chosen from among esters of a $C_8$–$C_{12}$ straight-chain dicarboxylic acid and a $C_3$–$C_6$ branched alcohol.

Advantageously, the $C_{12}$–$C_{15}$ alkyl ester of 2-hydroxypropanoic acid is chosen from among esters of a hydroxycarboxylic acid and a $C_{10}$–$C_{18}$ straight-chain alcohol.

In a preferred embodiment of the invention, the mixture of fatty esters contains 0 to 75% by weight of each of the said fatty esters, preferably in substantially equal proportions.

The invention also relates to a cosmetic product comprising a mixture of fatty esters as defined hereinbefore.

The following description, which has no limitative force, will enable the skilled man to understand the aim and advantages of the invention more clearly.

According to the invention a mixture of fatty esters for a cosmetic product comprises at least two fatty esters chosen from among esters of a $C_4$–$C_8$ branched monocarboxylic acid and a $C_8$–$C_{12}$ branched alcohol, esters of a $C_8$–$C_{12}$ straight-chain dicarboxylic acid and a $C_3$–$C_6$ branched alcohol, and esters of a hydroxycarboxylic acid and a $C_{10}$–$C_{18}$ straight-chain alcohol.

Completely unexpectedly, it has been discovered that a said formulation of a mixture of fatty acids can increase the sun protection factor (SPF) without also increasing the content of ultraviolet filtering products, as shown by the following examples:

EXAMPLE 1

Three sunscreen products 1, 2 and 3 were produced, each comprising the following in common and in the same quantities:
ethanol,
an ultraviolet filtering product A such as that sold by Messrs ROCHE under the commercial name PARSOL 1789, and
two ultraviolet filtering products B such as those sold by Messrs BASF under the commercial names UVINUL MBC95 and UVINUL T150.

The fatty ester in product No. 1 was 70% by weight of the isodecyl ester of 2,2-dimethyl propionic acid, also called isodecyl neopentanoate.

The fatty ester in product No. 2 was 70% by weight of the isopropyl ester of decanedioic acid, also called di-isopropyl sebacate.

Product No. 3 contained 70% by weight of a mixture of the two previously-mentioned fatty esters in the following proportions: 38% by weight of isodecyl neopentanoate and 32% by weight of di-isopropyl sebacate.

The sun protection factor (SPF) for each of these products was measured, showing that in product No. 3 the said factor had increased by 30% compared with product No. 1 and 25% compared with product No. 2.

EXAMPLE 2

A product No. 4 was produced, comprising the same common components as those in products 1, 2 and 3 in Example 1 plus 70% by weight of a mixture of fatty acids made up of 24% by weight of isodecyl neopentanoate, 23% by weight of di-isopropyl sebacate and 23% by weight of a $C_{12}$–$C_{15}$ alkyl ester of 2-hydroxypropanoic acid, also called $C_{12}$–$C_{15}$ lactate.

The sun protection factor (SPF) for product No. 4 was measured, showing an increase of 5% compared with product No. 3.

As these examples show, the association in accordance with the invention of fatty esters and ultraviolet filtering products very significantly increases the sun protection factor (SPF) of the resulting cosmetic product. There is therefore a synergistic effect.

The invention claimed is:

1. A sun shield product comprising: at least one ultraviolet filtering product and the combination of at least two fatty acid esters, said combination selected from the group consisting of:
   a) an isodecyl ester of 2, 2-dimethyl propionic acid;
   b) an isopropyl ester of decanedioic acid; and
   c) a $C_{12}$–$C_{15}$ alkyl ester of 2-hydroxypropanoic acid.

2. The product according to claim 1, wherein said product contains the combination of the isodecyl ester of 2, 2-dimethyl propionic acid, the isopropyl ester of decanedioic acid and the $C_{12}$–$C_{15}$ alkyl ester of 2-hydroxypropanoic acid.

3. The product according to claim 1, wherein it contains 0 to 75% by weight of each of said esters.

4. The product according to claim 1, wherein it contains said esters in substantially equal proportions.

5. A cosmetic substance for protection against the sun, wherein it comprises a product according to claim 1.

* * * * *